United States Patent
Tappehorn et al.

(10) Patent No.: US 12,409,293 B2
(45) Date of Patent: Sep. 9, 2025

(54) CONNECTION WITH A VOLUME FLOW SENSOR AND A HOMOGENIZATION UNIT FOR ARTIFICIAL VENTILATION OF A PATIENT AND MANUFACTURING PROCESS

(71) Applicant: Drägerwerk AG & Co. KGaA, Lübeck (DE)

(72) Inventors: Ludger Tappehorn, Lübeck (DE); Jan-Henning Lütkhoff, Lübeck (DE); Frerich Asmus, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 811 days.

(21) Appl. No.: 17/331,885

(22) Filed: May 27, 2021

(65) Prior Publication Data

US 2021/0370008 A1    Dec. 2, 2021

(30) Foreign Application Priority Data

May 29, 2020   (DE) ...................... 10 2020 114 507.1

(51) Int. Cl.
*A61M 16/08* (2006.01)
*A61M 16/00* (2006.01)

(52) U.S. Cl.
CPC .... *A61M 16/0816* (2013.01); *A61M 16/0057* (2013.01); *A61M 2016/0027* (2013.01);
(Continued)

(58) Field of Classification Search
CPC ...... A61M 16/0816; A61M 2016/0027; A61M 2016/003; G01F 5/005; F15D 1/0005; F15D 1/025; A61B 5/0876
See application file for complete search history.

(56) References Cited

U.S. PATENT DOCUMENTS 2,929,248 A * 3/1960 Sprenkle ................. G01F 15/00
138/40
3,645,298 A * 2/1972 Roberts ................. A61M 39/28
138/40
(Continued)

FOREIGN PATENT DOCUMENTS

CN            109745191 A     5/2019
DE     102007039537 A1 *   2/2009    ............ F15D 1/025
(Continued)

*Primary Examiner* — Kathryn E Ditmer
(74) *Attorney, Agent, or Firm* — McGlew and Tuttle, P.C.

(57) ABSTRACT

A connection device, for mechanical ventilation and monitoring of spontaneous breathing of a patient (P), includes a fluid-guiding unit (9, 11, 15) and establishes a fluid connection between a medical arrangement (100) and a patient-side coupling unit (19). A volume flow sensor (90) measures an indicator of volume flow of fluid through the fluid-guiding unit. A volume flow sensor component (2) engages with an interior of the fluid-guiding unit. A homogenization unit (10) is nonrotatably inserted into the interior between the patient-side coupling unit and the component and includes two sieves and a connection element, which connects the sieves together. The homogenization unit homogenizes the flow of fluid through the fluid-guiding unit. An inner profile of the fluid-guiding unit and an outer profile of the homogenization unit together form a mechanical coding, which determines a defined rotation position of the homogenization unit in relation to the fluid-guiding unit.

19 Claims, 6 Drawing Sheets

(52) U.S. Cl.
CPC ... *A61M 2016/003* (2013.01); *A61M 2207/00* (2013.01); *A61M 2230/40* (2013.01)

(56) References Cited

U.S. PATENT DOCUMENTS

| | | | |
|---|---|---|---|
| 3,733,898 A | 5/1973 | Yamamoto et al. | |
| 3,840,051 A * | 10/1974 | Akashi | F15D 1/025 |
| | | | 428/596 |
| 4,083,245 A * | 4/1978 | Osborn | A61B 5/08 |
| | | | 73/861.53 |
| 4,142,413 A * | 3/1979 | Bellinga | F15D 1/04 |
| | | | 73/198 |
| 4,280,360 A * | 7/1981 | Kobayashi | G01F 1/64 |
| | | | 138/40 |
| 4,993,269 A * | 2/1991 | Guillaume | G01F 1/36 |
| | | | 73/861.53 |
| 5,014,552 A * | 5/1991 | Kamiunten | G01F 1/6842 |
| | | | 73/198 |
| 5,253,517 A * | 10/1993 | Molin | G01F 1/684 |
| | | | 73/114.32 |
| 5,495,872 A * | 3/1996 | Gallagher | F15D 1/025 |
| | | | 138/40 |
| 5,695,644 A | 12/1997 | Buchanan et al. | |
| 5,762,107 A * | 6/1998 | Laws | F15D 1/025 |
| | | | 138/40 |
| 5,763,792 A * | 6/1998 | Kullik | A61B 5/087 |
| | | | 600/538 |
| 5,918,279 A * | 6/1999 | Hecht | F02M 35/10386 |
| | | | 73/204.21 |
| 7,024,945 B2 * | 4/2006 | Wallace | A61M 16/0051 |
| | | | 73/861.74 |
| 2004/0187871 A1 | 9/2004 | Kimmel et al. | |
| 2008/0246277 A1 * | 10/2008 | Gallagher | F16L 9/147 |
| | | | 285/148.13 |
| 2011/0201099 A1 | 8/2011 | Anderson et al. | |
| 2014/0048065 A1 * | 2/2014 | Haroutunian | F15D 1/001 |
| | | | 128/203.15 |
| 2014/0358022 A1 * | 12/2014 | Sansom | A61M 16/085 |
| | | | 600/537 |
| 2016/0370213 A1 * | 12/2016 | Stromsten | A61B 5/4836 |
| 2017/0216554 A1 | 8/2017 | Dunkel et al. | |
| 2017/0266399 A1 * | 9/2017 | Campana | A61M 16/107 |
| 2019/0151602 A1 | 5/2019 | Tappehorn et al. | |
| 2020/0022417 A1 | 1/2020 | Atkins et al. | |
| 2021/0372833 A1 | 12/2021 | Ming | |

FOREIGN PATENT DOCUMENTS

| | | | | |
|---|---|---|---|---|
| DE | 102008047511 A1 * | 3/2009 | | A61M 16/085 |
| DE | 102007052898 B3 | 4/2009 | | |
| DE | 102013018458 A1 | 5/2015 | | |
| DE | 102016014347 A1 | 6/2018 | | |
| DE | 102017000054 A1 | 7/2018 | | |
| DE | 102017202298 A1 | 8/2018 | | |
| DE | 102017004224 A1 | 11/2018 | | |
| DE | 102018000084 A1 | 7/2019 | | |
| DE | 102018003026 A1 | 10/2019 | | |
| EP | 2730293 A1 | 5/2014 | | |
| GB | 1328915 A | 9/1973 | | |
| KR | 101989844 B1 | 6/2019 | | |
| WO | 02052230 A1 | 7/2002 | | |
| WO | WO-2004025226 A1 * | 3/2004 | | F15D 1/02 |
| WO | 2016032457 A1 | 3/2016 | | |
| WO | 2018132483 A1 | 7/2018 | | |
| WO | WO-2019213750 A1 * | 11/2019 | | B01F 25/4316 |

* cited by examiner

CONNECTION WITH A VOLUME FLOW SENSOR AND A HOMOGENIZATION UNIT FOR ARTIFICIAL VENTILATION OF A PATIENT AND MANUFACTURING PROCESS

CROSS REFERENCE TO RELATED APPLICATIONS

This application claims the benefit of priority under 35 U.S.C. § 119 of German Application 102020114507.1, filed May 29, 2020, the entire contents of which are incorporated herein by reference.

TECHNICAL FIELD

The present invention pertains to a connection device for the mechanical ventilation and/or for the monitoring of the spontaneous breathing of a patient. At least from time to time, such a connection device connects a ventilator for mechanical ventilation or a patient monitor for monitoring with a patient-side coupling unit. The patient-side coupling unit is connected to the patient for the duration of a treatment and comprises, for example, a breathing mask that is placed on the face of the patient, or a tube that is inserted into the trachea of the patient, or a mouthpiece. Such a connection device comprises a fluid-guiding unit which is capable of sending a fluid from the ventilator to the patient-side coupling unit and optionally also in the opposite direction or from the patient-side coupling unit to the patient monitor, especially a hose. The fluid comprises breathing air and may be enriched with anesthesia gas. The present invention pertains, furthermore, to a process for the manufacture of such a connection device.

TECHNICAL BACKGROUND

Such connection devices and/or patient-side coupling units are known from DE 10 2018 000 084 A1, U.S. Pat. No. 2,929,248 A, DE 10 2013 018 458 A1, DE 10 2007 052 898 B3, DE 10 2016 014 347 A1, DE 10 2018 003 026 A1, DE 10 2017 004 224 A1 and DE 10 2017 000 054 A1.

A volume flow sensor is used, in particular, to monitor the vital functions of the patient and/or to control and/or to regulate the ventilator. Such a volume flow sensor measures the volume flow of fluid through the fluid-guiding unit. The volume flow is an indicator of the volume per time unit. This volume flow is, as a rule, variable over time. Use conditions and environmental effects often make a reliable measurement of the volume flow difficult.

SUMMARY

A basic object of the present invention is to provide a connection device for a medical device, especially for the mechanical ventilation and/or for the monitoring of the spontaneous breathing of a patient, wherein the connection device comprises a fluid-guiding unit and a volume flow sensor and makes it possible to do a more reliable measurement of the volume flow in the fluid-guiding unit than prior-art connection devices.

The connection device according to the present invention is configured for being used for a medical arrangement, especially for a medical arrangement for the mechanical ventilation, for the anesthetization and/or for the monitoring and measurement of the intrinsic breathing activity of a patient. The intrinsic breathing activity results from the spontaneous breathing and/or from a stimulated activity of the respiratory muscles of the patient. This patient can be fully narkotisated, so that he/she is being mechanically ventilated exclusively. It is also possible that the connection device according to the present invention is used to monitor and/or to measure the intrinsic breathing activity of the patient. Further, it is possible that the mechanical ventilation and the intrinsic breathing activity overlap. It is also possible that the intrinsic breathing of the patient is stimulated externally and the overlapping of spontaneous and externally stimulated breathing shall be monitored.

The connection device according to the present invention comprises a fluid-guiding unit which may be configured as a hose (smooth hose or pleated hose) or a tube or may comprise at least one hose and/or one tube. This fluid-guiding unit is capable of establishing a fluid connection between a patient-side coupling unit and a medical device. The patient-side coupling unit can be detachably connected to a patient and especially comprises a face mask, which can be placed onto the face of a patient, and/or a tube, which can be inserted into the body of the patient. The medical device is especially a ventilator, an anesthesia apparatus or a patient monitor. The fluid-guiding unit thus comprises a patient-side end, at which the fluid-guiding unit is connected or can be connected to the patient-side coupling unit, and a device-side end, at which the fluid-guiding unit is connected or can be connected to a medical device directly or via an intermediate unit.

The connection device comprises, furthermore, a volume flow sensor. This volume flow sensor is capable of measuring an indicator of the volume flow of fluid through the fluid-guiding unit, i.e., a variable, which correlates with the volume flow. The volume flow is the volume per time unit of the fluid flow. This volume flow sensor comprises a component, which engages (meshes) with the interior of the fluid-guiding unit. Fluid, which flows through the fluid-guiding unit, flows past this engaging component and/or through this engaging component. A measurable parameter of this fluid flow correlates with the volume flow and influences this engaging component.

Furthermore, the connection device comprises a homogenization unit, which is preferably a purely mechanically active component. This homogenization unit is capable of homogenizing the flow of fluid through the fluid-guiding unit. This homogenization unit is inserted into the interior of the fluid-guiding unit, especially in a nonrotatable manner, i.e., the homogenization unit cannot be rotated in relation to the fluid-guiding unit. The homogenization unit preferably does not change its position in relation to the fluid-guiding unit, while the volume flow sensor is inserted. The homogenization unit is inserted at a position, which is located between the patient-side end of the fluid-guiding unit and thus between the patient-side coupling unit, on the one hand, and the engaging component of the volume flow sensor, on the other hand. The homogenization unit is positioned and inserted into the interior of the fluid-guiding unit such that fluid, which flows from the patient-side coupling unit through the fluid-guiding unit to the engaging component or in the opposite direction, has to flow through the homogenization unit and cannot bypass this unit. Of course, this only applies to an intact connection device and especially to a fluid-guiding unit without a leak.

The homogenization unit comprises two sieves and a connection element. The connection element connects the two sieves mechanically permanently to one another (fixedly connects the two sieves to one another). In particular, the one sieve may not, as a result, be rotated in relation to the other sieve, or the distance between the sieves may not be changed. Viewed in the direction of flow of the fluid through the fluid-guiding unit, the two sieves are arranged behind one another and spaced apart from one another.

The connection device may be exposed to different ambient conditions during use. Various copies of a connection device according to the present invention may be connected to different patient-side coupling units, so that different profiles of the fluid flow are formed. An actual dimension or position of a component of the connection device may deviate from a position predefined by the construction, e.g., because of production inaccuracies. Nevertheless, the volume flow sensor shall yield reliable measured values. Therefore, it is desired that flowing in and/or flowing through the engaging component be relatively homogeneous and that the flowing in or flowing through can be reproduced. An ideal homogenization means that at a point in time the volume flow does not vary over the location, and especially not in a direction at right angles to the flow direction of the fluid. Thus, the higher the homogenization, the less the volume flow varies with the location. Of course, an ideally homogenized fluid flow may also vary with time, for example, because of spontaneous breathing of a patient or because of ventilation strokes of a connected ventilator.

A high degree of homogenization is especially desirable for the following reason: The engaging component of the volume flow sensor shall make possible a measurement of the volume flow, but shall not influence the volume flow significantly. Therefore, the engaging component engages, as a result, only in a defined area of the length and of the cross-sectional area of the fluid-guiding unit, i.e., not over the entire length and cross-sectional area. The fluid-guiding unit is moved and bent and possibly shaken during the use. Nevertheless, the volume flow shall be able to be measured in a reliable manner. This requires a sufficiently high level of homogenization.

Each sieve of the homogenization unit increases the degree of homogenization of the fluid flow, as compared with a device without sieve. The fluid may flow through the sieve only at defined points. Up to a certain degree, each sieve of the homogenization unit therefore smoothens sudden changes over time and/or in space in the volume flow.

According to the present invention, the homogenization unit comprises two sieves arranged behind one another in the flow direction. This configuration leads to a better homogenization than if only a single sieve were present. The fluid flow can calm down in the space between the two sieves, and especially in case of the fluid flow in each of the two opposite flow directions.

The volume flow sensor is adjusted, as a rule, before a use of the connection device, for example, for a defined type or a defined series or a defined production batch of sensors and/or connection devices and/or medical devices. The use conditions and ambient conditions during a use of the connection device may vary and deviate from the conditions occurring during the adjustment. Nevertheless, each copy of the volume flow sensor shall largely yield the same results during the use as during the adjustment. Results shall be able to be reproduced.

In a preferred embodiment, an inner profile of the fluid-guiding unit and an outer profile of the homogenization unit together form a mechanical coding. This mechanical coding specifies n possible defined rotation positions of the homogenization unit in relation to the fluid-guiding unit, wherein $n \geq 1$. Especially preferably n=1, i.e., the homogenization unit may occupy only a single rotation position in relation to the fluid-guiding unit.

The mechanical coding contributes to the homogenization unit being inserted into the fluid-guiding unit on the inside in a defined rotation position and thus in a defined manner. This makes it easy to adjust a type or batch of connection devices by means of a copy or a few copies of the volume flow sensor and to use the adjusted volume flow sensor for a larger number of copies of the connection device according to the present invention. Without such a mechanical coding, there is the risk that the homogenization unit is used differently in different copies of a connection device, which may have an effect on the measurement results of the volume flow sensor and hence may significantly change and therefore distort the measurement results compared to the adjustment.

Since the homogenization unit is inserted into the fluid-guiding unit in a defined rotation position, and the mechanical coding specifies this rotation position, this rotation position is always the same for each connection device according to the present invention (each copy). Therefore, the homogenization unit can in many cases be manufactured with a greater production tolerance than if different rotation positions were possible. It is not necessary that a sieve and especially the recesses therefore be configured in a precisely rotationally symmetrical manner to a central axis of the sieve. In particular, it is not necessary thanks to the present invention for the holes or other recesses in a sieve of the homogenization unit to form a precisely rotationally symmetrical hole pattern.

The effect that the homogenization unit does not need to be manufactured in a precisely rotationally symmetrical manner has the following advantage: In case it would be necessary to manufacture the homogenization unit in a rotationally symmetrical manner, a complicated checking would be necessary in many cases after the production to determine whether the homogenization unit is actually rotationally symmetrical. In many cases, a higher number of homogenization units would be treated as rejects, since these are not sufficiently precisely rotationally symmetrical. The mechanical coding according to the present invention avoids this drawback, because the hole pattern does not necessarily have to be rotationally symmetrical.

Each sieve preferably extends in a plane. This plane is at right angles to or at an angle to the flow direction of the fluid through the fluid-guiding unit.

According to a preferred embodiment, an outer profile of the homogenization unit and an inner profile of the fluid-guiding unit together form the mechanical coding. In one embodiment, the outer profile of at least one sieve deviates from an ideal circle. The largest diameter of the sieve in the plane, in which the sieve extends, is preferably at least 10%, preferably at least 20%, greater than the smallest diameter in this plane.

In one configuration, the outer profile of an eccentric, i.e., non-circular sieve of the homogenization unit together with the inner profile of the fluid-guiding unit forms the mechanical coding, and the outer profile of the other sieve is circular.

In one embodiment of this configuration, at least one sieve of the homogenization unit, preferably precisely one sieve, has an outer profile with the following properties: A cross section through the outer profile of the sieve, i.e., a cross section in the plane, in which the sieve extends, comprises at least one circular segment as well as at least one flattened segment. The flattened segment or one flattened segment may be, e.g., a line or a segment of an ellipse. An area of the fluid-guiding unit has a corresponding inner profile at least at a point, at which the homogenization unit is positioned. The outer profile with the circular segment and the flattened segment as well as the corresponding inner profile form the mechanical coding or form a component of the mechanical coding.

In one embodiment, at least one sieve comprises a projection that protrudes outwards, for example, a bead. An inner profile of the fluid-guiding unit comprises a corresponding recess, for example, a groove. The projection of the sieve engages with the recess of the inner profile. The projection and the recess together form the mechanical coding or are a component of the mechanical coding.

In one embodiment, the fluid-guiding unit comprises a bent fluid-guiding element and a linear fluid-guiding unit. The bent fluid-guiding element is located between the patient-side coupling unit and the linear fluid-guiding element. In many cases such an embodiment is advantageous, so that the connection device is compressed, stretched, expanded or twisted relatively little. The engaging component of the volume flow sensor engages with the interior of the linear fluid-guiding element. The homogenization unit is inserted into the interior of the bent fluid-guiding unit.

As a rule, more intense swirls occur in a bent fluid-guiding element than in a linear fluid-guiding element. The homogenization unit reduces the effect of such swirls on the measurement results of the volume flow sensor.

According to the present invention, each sieve comprises a set of a plurality of recesses through which fluid can flow. These recesses are designated as holes below. The holes may have, e.g., the shape of circles or ellipses or polygons. It is possible that the holes of a sieve all have the same shape and are especially of the same size. It is also possible that the holes of at least one sieve have different shapes and/or dimensions.

At least one sieve has an inner area and an outer area in another embodiment. The designations "inner area" and "outer area" refer to the central axis of the sieve. This central axis is at right angles to the plane, in which the sieve extends and extends parallel to or at an angle to the flow direction of the fluid. The inner area is traversed by a first set, which comprises a plurality of holes, and the outer area is traversed by a second set, which likewise comprises a plurality of holes. The maximum dimension of a hole of the first set is greater than the maximum dimension of a hole of the second set. Hence, this configuration especially contributes to a better homogenization, because more intense swirls often occur in the outer area, i.e., close to the inner wall of the fluid-guiding unit, than in the inner area. It is also possible that no holes at all are present in an outer area of a sieve, i.e., close to the inner wall of the fluid-guiding unit.

In one embodiment, at least one stop element is mounted in the interior of the fluid-guiding unit. This stop element limits a possible movement of the homogenization unit towards the patient-side coupling unit. In this embodiment, a minimal distance is maintained between the homogenization unit and the patient-side coupling unit, which is often desired. Moreover, this feature facilitates the manufacture of a connection device according to the present invention, because the homogenization unit can be pushed from one end into the fluid-guiding unit until the homogenization unit comes into contact with the stop element.

The elements of the homogenization unit may consist of different materials. The elements may be manufactured separately from one another and then be assembled into the homogenization unit. In one preferred embodiment, the homogenization unit is, by contrast, configured as a single, one-piece component and is especially continuously manufactured from the same material. Especially preferably, the homogenization unit is even a monolithic component, i.e., a component, which is manufactured in a single manufacturing step. The homogenization unit is preferably manufactured by molding, for example, by injection molding.

In one embodiment, the volume flow sensor measures an indicator of a pressure difference, namely the difference between two pressures at different points in the fluid-guiding unit and preferably at the same time—stated more precisely: At two times, between which the time period lies, in which the gas flows from the one point to the other point. The pressure difference correlates with the sought volume flow. The volume flow sensor is capable of analyzing a connection between the pressure difference and the volume flow, and this connection is preferably stored in a memory in a computer-accessible manner. The connection may be a characteristic curve. This connection is determined empirically beforehand in an adjustment phase and is used in each use. At least one copy of the connection device according to the present invention is used in this adjustment phase. The present invention reduces the risk that the actual connection between the volume flow and the pressure difference deviates significantly from the connection, which has been determined in the adjustment phase, during a use.

The volume flow sensor according to this embodiment comprises a pressure-measuring unit as well as two pneumatic lines. Each pneumatic line establishes a respective fluid connection between the fluid-guiding unit and the pressure-measuring unit. Each pneumatic line branches off from the fluid-guiding unit at a respective branching-off point. The two branching-off points, viewed in a flow direction of fluid through the fluid-guiding unit, are spaced apart from one another, i.e., are arranged behind one another, viewed in the flow direction. Because of this feature, an indicator of the difference between the two pressures in the two pneumatic lines, more precisely: An indicator of the pressure difference, can be measured in the fluid-guiding unit. This pressure difference is, as a rule, variable over time, and the pressure-measuring unit measures the indicator of the pressure difference repeatedly, for example, with a predefined scanning frequency.

In one embodiment, the connection device according to the present invention can be manufactured by a 3D printer producing at least the following components of this connection device: The fluid-guiding unit, the homogenization unit and preferably the engaging component of the volume flow sensor. A computer program is capable of actuating this 3D printer and thereby ensure that the 3D printer produces these components of the connection device according to the present invention. In particular, an analysis unit of the volume flow sensor is preferably manufactured in a different way. The connection device according to the present invention is assembled from the components, which were produced by 3D printing, and optionally additional components. In some cases, a connection device can be manufactured rapidly in this manner, which meets predefined boundary conditions, especially with regard to geometric properties. It is also possible that a plurality of 3D printers each print out at least one component of the connection device according to the present invention, even at different locations.

The connection device according to the present invention may be a component of a medical device, wherein this medical device is configured for mechanically ventilating a patient and/or monitoring and measuring the spontaneous breathing of this patient, optionally an overlap of spontaneous breathing and stimulated breathing. The medical device comprises a medical device, especially a ventilator or a patient monitor, a patient-side coupling unit as well as a connection device according to the present invention. An anesthesia apparatus is a special case of a ventilator. The connection device establishes at least from time to time a fluid connection between the patient-side coupling unit and the medical device. The patient-side coupling unit is coupled with the patient at least from time to time. The measurement results of the volume flow sensor are used for controlling and for regulating the ventilation strokes of the ventilator in the case of mechanical ventilation. In case the connection device is connected to an anesthesia device, then the measurement results of the volume flow sensor can also be used for measuring an indicator of the quantity of an anesthetic which is fed to the patient by means of the fluid-guiding unit.

In a preferred embodiment, a connection device according to the present invention is manufactured as follows:

The volume flow sensor is manufactured or formed. This volume flow sensor comprises the engaging component.

The homogenization unit is manufactured or formed. The homogenization unit is preferably manufactured as a one-piece component, especially preferably monolithically, especially by injection molding or another molding process.

A fluid-guiding element, which functions as a patient-side connection unit, and an additional fluid-guiding element are manufactured or formed. The patient-side connection unit is connected to a patient-side coupling unit or can be connected to a patient-side coupling unit after the manufacture or during the formation.

The engaging component of the volume flow sensor is inserted into the additional fluid-guiding element. After the insertion, the engaging component engages with the additional fluid-guiding element.

The homogenization unit is inserted on the inside into the patient-side connection unit. It is preferably pushed in, namely preferably from the end, which is facing away from the patient-side coupling unit. The homogenization unit is especially preferably inserted until it reaches a stop element in the interior of the patient-side coupling unit. The stop element reduces the risk that the homogenization unit is inserted too far, i.e., is positioned too close to the patient-side coupling unit. The mechanical coding ensures that the homogenization unit is inserted with the correct rotation position.

After the homogenization unit is inserted, the patient-side connection unit is connected in a fluid-tight manner to the additional fluid-guiding element.

The patient-side connection unit and the additional fluid-guiding element together form the fluid-guiding unit or belong to this fluid-guiding unit.

In a preferred embodiment, the patient side connection unit is bent or comprises a bent segment. The homogenization unit is inserted until it reaches the bent segment. The additional fluid-guiding element is preferably a flexible hose (smooth hose or pleated hose) or a rigid tube. The expansion of the patient-side connection unit, viewed in the fluid flow direction, is preferably less than half as great as the expansion of the additional fluid-guiding element. As a result, the volume flow sensor is positioned close to the patient-side coupling unit and thus close to the patient. This feature makes it possible to measure the volume flow close to the patient, which is desired, as a rule.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
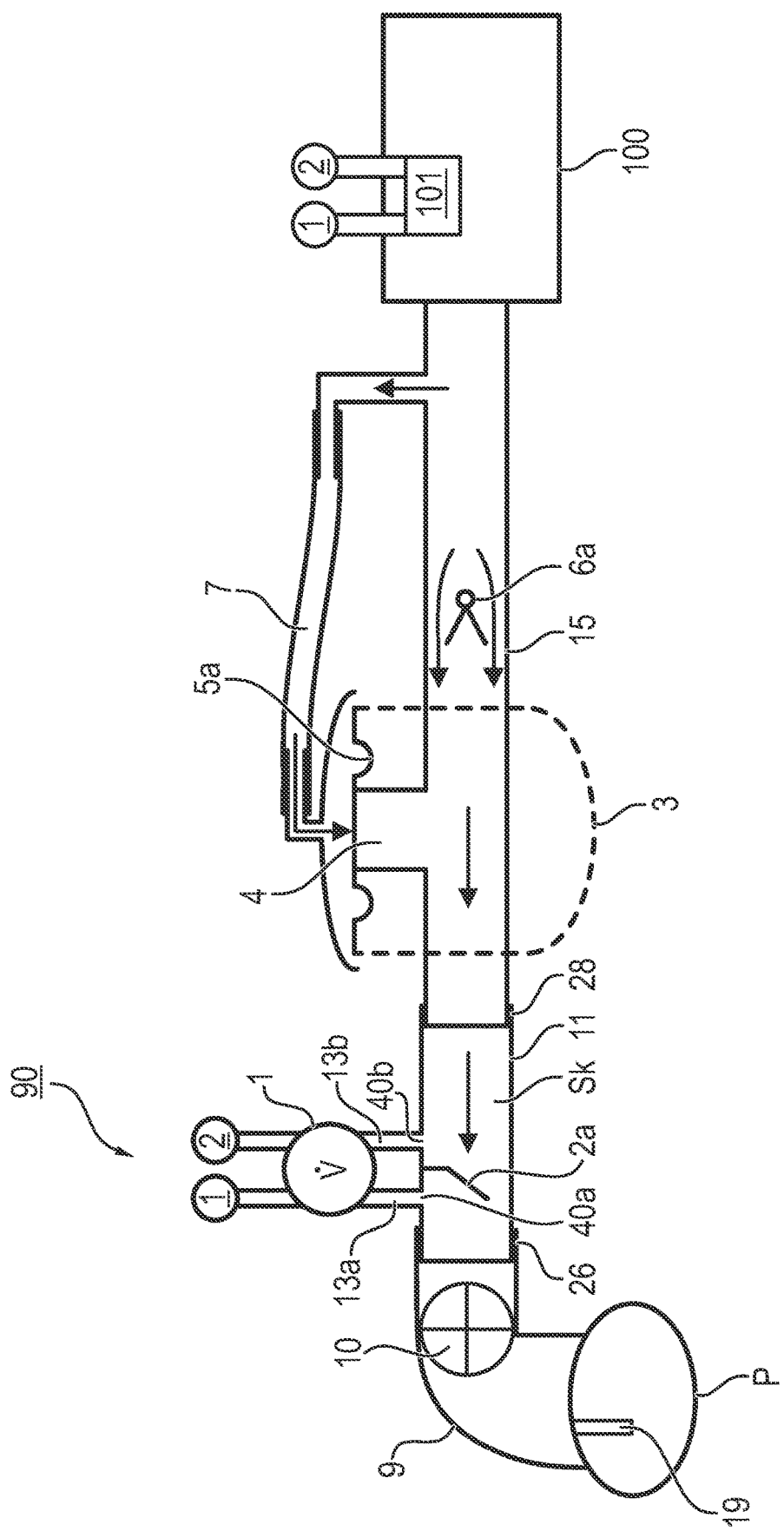
FIG. 1 is a schematic view showing the ventilation circuit in case of an inhalation (inspiration) of the patient.

Referring to the drawings, in the exemplary embodiment, the present invention is used for mechanical ventilation of a patient P. A ventilator 100 assists and replaces the spontaneous breathing of the patient P. The patient P is mechanically ventilated using the present invention during a transport in one embodiment. The ventilator 100 may be configured according to one of the number of products offered by Drager under the trademark name Oxylog®, which are capable of ventilating a patient P during a transport. The ventilator 100 may also be configured as an anesthesia apparatus, which anesthetizes the patient P.

In the exemplary embodiment, a ventilation circuit is established between the patient P and the ventilator 100, i.e., fluid flows not only from the ventilator 100 to the patient P, but also back from the patient P in the direction of the ventilator 100. The present invention can also be used for a connection device, in which fluid flows only from the ventilator 100 to the patient P, but not in the other direction.

Figure 2:
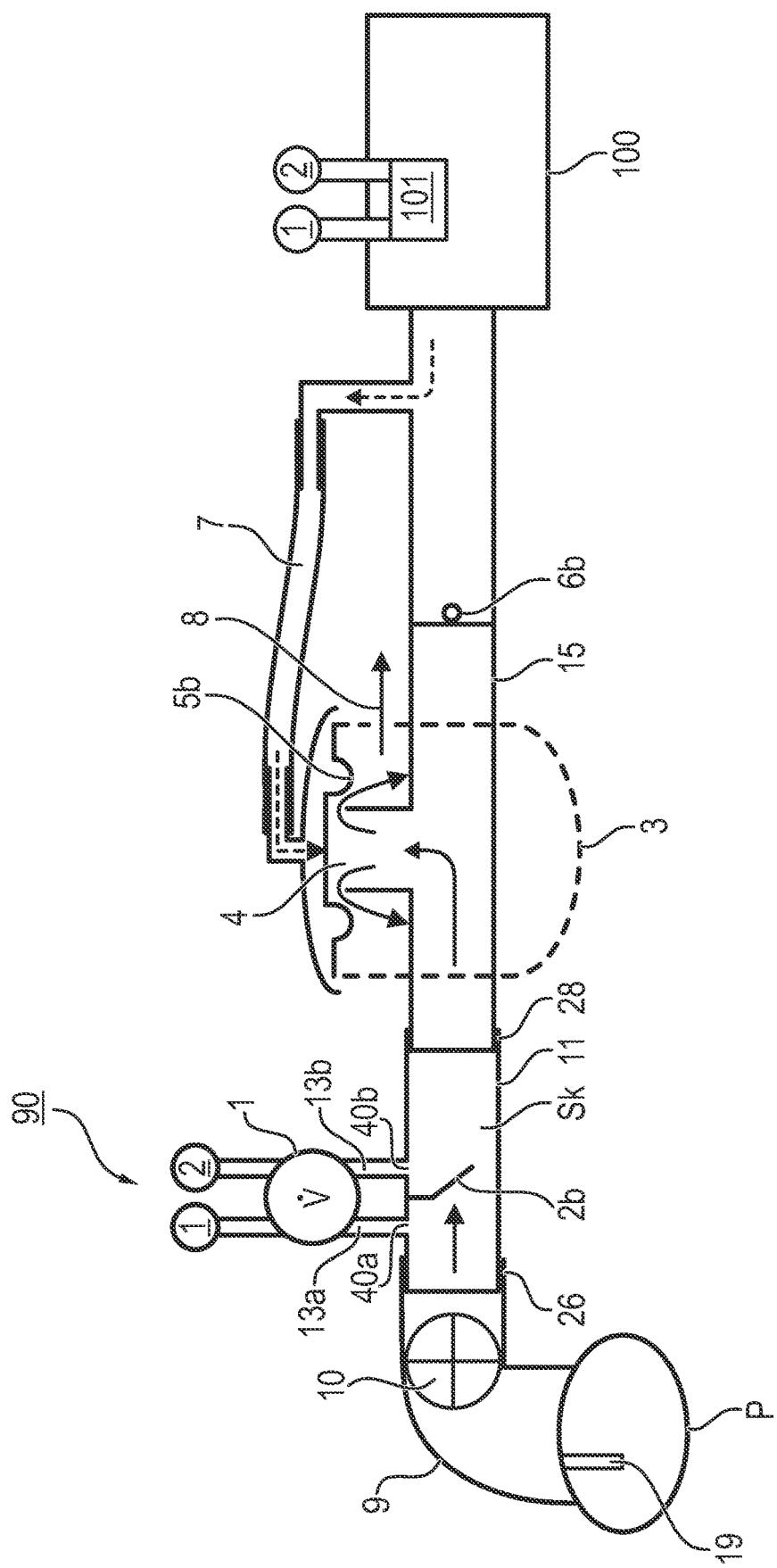
FIG. 2 is a schematic view showing the ventilation circuit in case of an exhalation (expiration) of the patient.

FIG. 1 shows an exemplary ventilation circuit between the patient P and the ventilator 100 during an inhalation (inspiration) of the patient. The ventilator 100 feeds to the patient P breathing air or a mixture of a carrier gas and an anesthetic or another fluid. The flow direction, which is suggested by arrows, is shown in the view, i.e., from right to left. FIG. 2 shows the ventilation circuit from FIG. 1 during an exhalation (expiration), in which the patient P exhales breathing air. The flow direction is thus shown from left to right.

The ventilation circuit comprises the following components:

a patient-side coupling unit in the form of a tube 19 in the trachea of the patient P or a breathing mask, not shown, on the face of the patient P, an angular, hollow, patient-side connection unit 9, which is preferably manufactured from a transparent material, a rigid tube 11, which is preferably likewise manufactured from a transparent material, a flexible hose 15, an exhalation valve 3 in the hose 15, which comprises a feed opening 4 and a discharge opening 8 (cf. FIG. 2), a diaphragm 5 in the exhalation valve 3, a recoil diaphragm 6 in the hose 15, and a pneumatic control line 7 from the hose 15 to the exhalation valve 3.

The hose 15 is connected in a fluid-tight manner to the ventilator 100 and in a fluid-tight manner to the tube 11. The tube 11 is connected in a fluid-tight manner to the patient-side connection unit 9. The patient-side connection unit 9 is connected in a fluid-tight manner to the patient-side coupling unit 19. The patient-side connection unit can preferably be rotated about the central axis of the tube 11 relative to the tube 11. The patient-side connection unit 9, the tube 11 and the hose 15 together form the fluid-guiding unit of the exemplary embodiment.

The diaphragm 5 in the exhalation valve 3 can be brought into a closed position 5a (FIG. 1) and into an open position 5b (FIG. 2). Even in the open position 5b, the diaphragm 5 ensures that an end-expiratory minimum pressure (PEEP), which is a pressure which remains after an exhalation process, is maintained in the lungs of the patient P. A sufficiently high end-expiratory pressure reduces the risk that the lungs of the patient P will collapse or that a different barotrauma will occur. The recoil diaphragm 9 can be brought into an open position 6a (FIG. 1) and into a closed position 6b (FIG. 2).

During the inspiration (FIG. 1), the ventilator 100 presses a fluid, for example, breathing air, into the hose 15 to the patient P. As a result, the recoil diaphragm 6 is opened (position 6a). Moreover, air, which the ventilator 100 discharges, is pressed through the pneumatic control line 7, as a result of which the diaphragm 5 is brought into the closed position 5a. The fluid reaches the patient P via the tube 11, the patient-side connection unit 9 and the patient-side coupling unit 19.

During the expiration (FIG. 2), air is moved from the patient P towards the ventilator 100 through the patient-side coupling unit 19, the patient-side connection unit 9, the tube 11 and the hose 15. The recoil diaphragm 6 is in the closed position 6b. The exhalation valve 3 sends exhaled air to the diaphragm 5, which is transferred into the open position 5b.

The respective flow direction of fluid is shown by arrows in FIG. 1 and FIG. 2.

In the example being shown, the recoil diaphragm 6 is opened and closed pneumatically. It is also possible that the ventilator 100 actuates an actuator and the actuator opens and closes the recoil diaphragm 6.

In the exemplary embodiment, the volume flow (volume per time unit) of fluid, which flows to the patient P and from the patient P, shall be measured continuously both during the inspiration and during the expiration. Therefore, a volume flow sensor 90 is arranged in the ventilation circuit. This volume flow sensor 90 comprises in the exemplary embodiment a measuring cuvette with a diaphragm 2, which is arranged close to the patient-side end of the tube 11, cf. FIG. 3, a pressure-measuring unit 101, which is arranged in the ventilator 100, two pneumatic lines 13a and 13b, which lead from the measuring cuvette 2 to the pressure-measuring unit 101 and branch off from the tube 11 in two branching-off points (openings) 40a and 40b, and a display unit 1 close to the measuring cuvette 2.

Because the pressure-measuring unit 101 is arranged in the ventilator 100, it does not need its own power supply and is protected better against mechanical and other ambient conditions than in another possible position.

The diaphragm 2 is mounted at the inner wall of the tube 11 in a position, which is located between the two branching-off points 40a and 40b, in which the two lines 13a and 13b branch off from the tube 11. The diaphragm 2 is fastened to the tube 11 on one side and therefore can be moved like a lug back and forth in relation to the tube 11 between an inspiration position 2a (FIG. 1) and an expiration position 2b (FIG. 2). Fluid, which flows through the tube 11, moves the diaphragm 2. If no fluid flow occurs in the tube 11, then the surface of the diaphragm 2 is approximately at right angles to the inner wall of the tube 11.

Thanks to the diaphragm 2, a difference occurs between the pressures in the two lines 13a and 13b. Thanks to the two lines 13a and 13b, this pressure difference is present at the pressure-measuring unit 101 as well. The pressure-measuring unit 101 measures this present pressure difference. The measured pressure difference correlates with the sought volume flow. The pressure-measuring unit 101 measures this pressure difference. Thanks to the diaphragm 2, the connection between the occurring pressure difference and the sought volume flow can be sufficiently precisely described in many cases by a linear connection, i.e., by a characteristic curve, or by a traverse. A plurality of parameters, which specify this characteristic curve or this traverse, are stored in a memory, not shown, of the pressure-measuring unit 101. The position of a display element of the display unit 1 correlates with the difference between the pressures in the two lines 13a and 13b. A scale of the display unit 1 displays the volume flow, which corresponds to this pressure difference.

Figure 3:
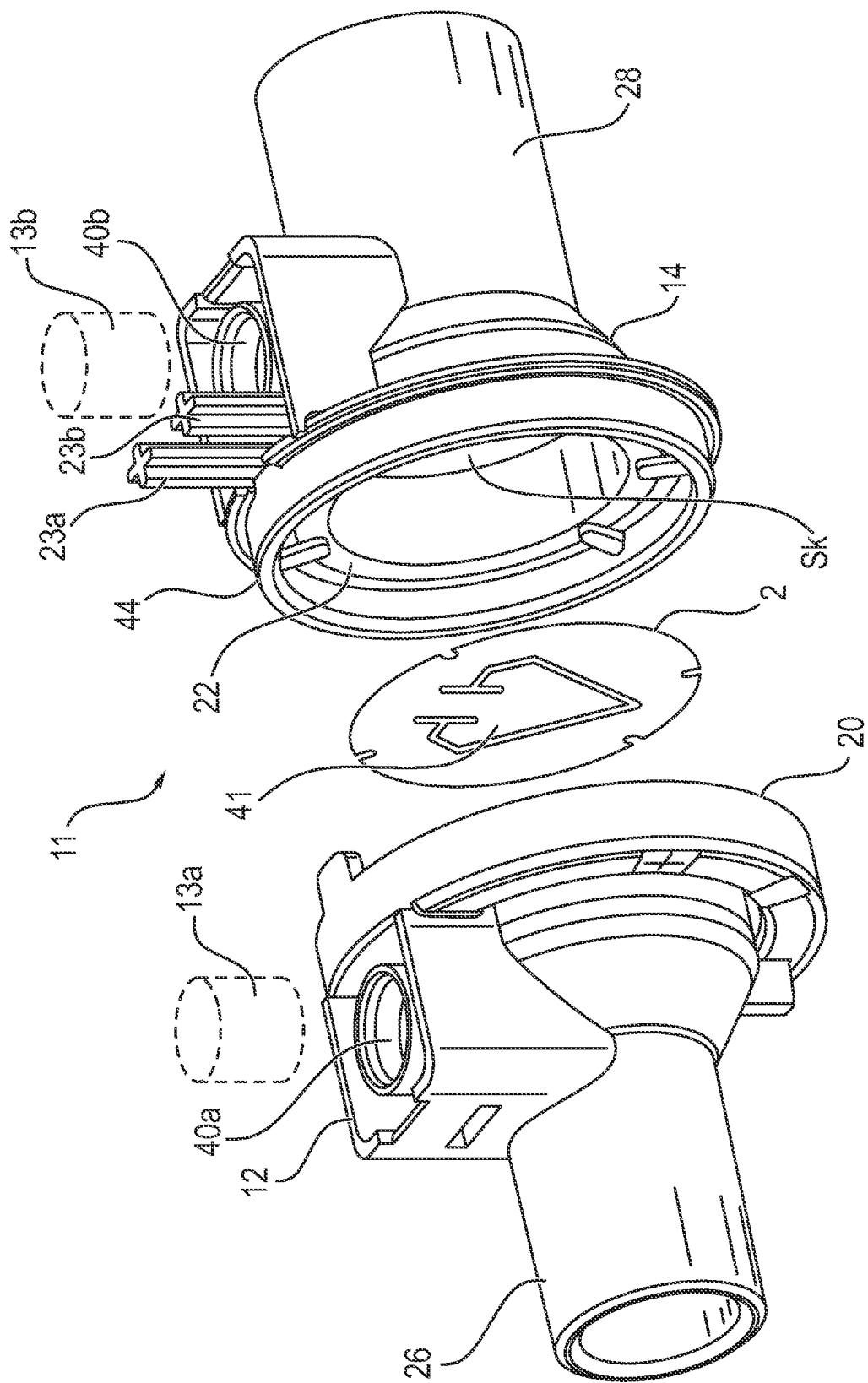
FIG. 3 is a perspective view showing how the diaphragm of the volume flow sensor is installed into the tube.

FIG. 3 shows the diaphragm 2, an arrow-shaped recess 41 in the diaphragm 2, a segment each of the two pneumatic lines 13a and 13b as well as two sections 26, 28 of the tube 11. The diaphragm 2 is arranged in a housing with the two housing halves 12 and 14. The patient-side housing half 12 (on the left) is connected in a fluid-tight manner to the tube section 26, and the ventilator-side housing half 14 is connected in a fluid-tight manner to the tube section 28. In the example shown, the tube section 26 engages with the connection unit 9 from the inside, and the tube section 28 encloses the hose 15 from the outside. It is also possible that, conversely, the tube section 26 encloses the connection unit 9 from the outside and the tube section 28 engages with the hose 15 from the inside or both tube sections 26, 28 enclose from the outside or mesh from the inside.

Each housing half 12, 14 comprises a respective flange area with a connection surface 20 and 22, respectively. The two connection surfaces 20 and 22 face one another and enclose the diaphragm 2 between them. A circumferential projection 44 at the housing half engages with a corresponding circumferential recess, not shown, at the housing half 12. The two tube sections 26 and 28 and the two housing halves 12 and 14 belong to the tube 11. When the two housing halves 12 and 14 are connected to one another, they together form a housing, which encloses the diaphragm 2 in a fluid-tight manner. A flow duct Sk leads through the two tube sections 26 and 28 and the two housing halves 12 and 14. Such a device as well as a process for manufacturing such a device are described in DE 10 2018 000 084 A1.

The two lines 13a and 13b begin in a cap, not shown, and lead to the pressure-measuring unit 101. This cap can be placed onto the tube 11 when the two housing halves 12, 14 are connected to one another. Two guide elements 23a and 23b guide the cap into a desired position during placement thereof. In this desired position, the opening 40a in the tube section 26 leads into the line 13a. The opening 40b in the tube section 28 leads into the line 13b.

The flow of fluid through the tube 11 is influenced by different ambient conditions, which are, as a rule, variable over time, as well as by the arrangement of the patient-side connection unit 9 and of the tube 11 in relation to the patient P. Nevertheless, the volume flow sensor 90 shall measure the volume flow through the tube 11 with relatively high reliability. Therefore, a homogenization unit 10 is arranged in the interior of the patient-side connection unit 9, namely in a position between the patient P and the measuring cuvette 2. This homogenization unit 10 homogenizes the flow of fluid through the patient-side connection unit 9, especially both during the inspiration and during the expiration. "Homogenization" of a fluid flow is defined by the variation over time of the quantity per time unit and the variation over time of the direction of fluid flow being reduced automatically.

Figure 4B:
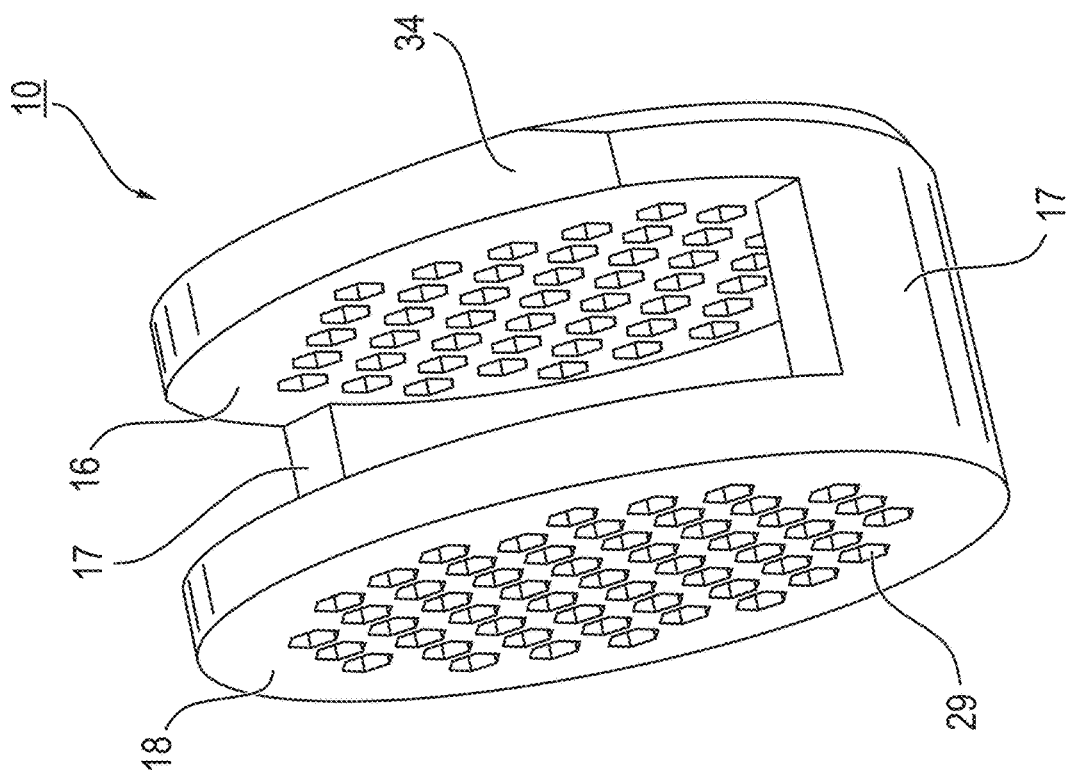
FIG. 4B is a perspective view showing the homogenization unit from another viewing direction.
Figure 4A:
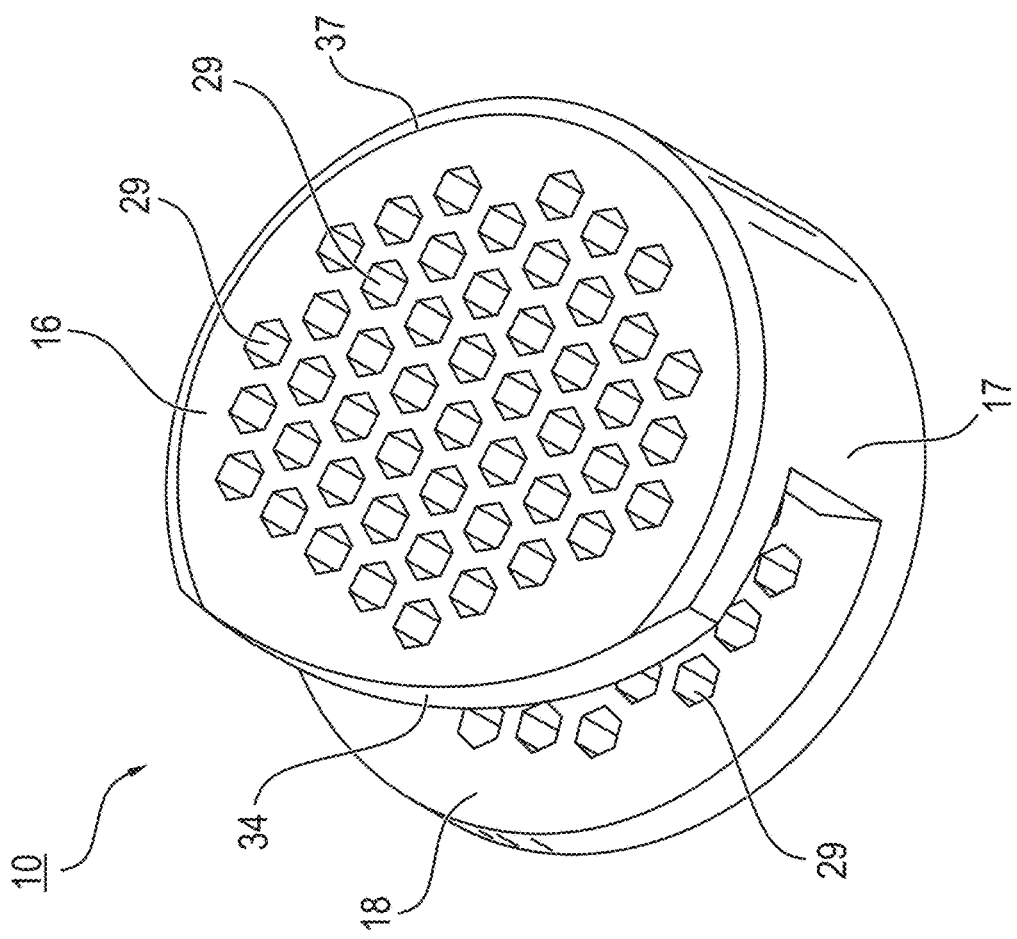
FIG. 4A is a perspective view showing the homogenization unit from one viewing direction.

FIG. 4 shows a possible embodiment of the homogenization unit 10 in two perspective views from two different viewing directions. The homogenization unit 10 is preferably manufactured from plastic by injection molding or by 3D printing, preferably in one piece as a single component, and has a light color and preferably a white or milky color. The homogenization unit 10 is, as a result, visible from the outside through the wall of the transparent patient-side connection unit 9. Therefore and because of the white color, deposits on the homogenization unit 10 can be detected visually, without the homogenization unit 10 having to be pulled out. The homogenization unit 10 or at least the sieves 16 and 18 may also be manufactured from metal.

The homogenization unit 10 comprises
a smaller sieve 16,
a larger sieve 18 and
a connection unit 17, which permanently connects the two sieves 16 and 18 to one another.

The two sieves 16 and 18 extend in two planes, which are parallel to one another and which are at right angles to the flow direction of the fluid through the patient-side connection unit 9 in the exemplary embodiment. The minimal dimension of the smaller sieve 16 in its plane is smaller than the minimal dimension of the larger sieve 18 in its plane. In the exemplary embodiment, both sieves 16 and 18 have the same maximum dimension. The two sieves 16, 18 may have the same thickness or different thicknesses.

A respective set of holes is prepared in each sieve 16, 18. These holes may be round or polygonal. In the example from FIG. 4, the holes are hexagonal. The hole patterns of the two sieves 16, 18 are also approximately hexagonal and form each a honeycomb structure. Apart from this hexagonal hole pattern, each sieve 16, 18 has an area, which is free from holes.

The respective outer profile of each sieve 16, 18 is preferably positioned flush at the inner wall of the patient-side connection unit 9, so that no gap occurs and the outer profile adjoins the inner profile in a fluid-tight manner. Such a gap could cause swirls, which could distort a measurement result of the volume flow sensor 90.

Figure 5:
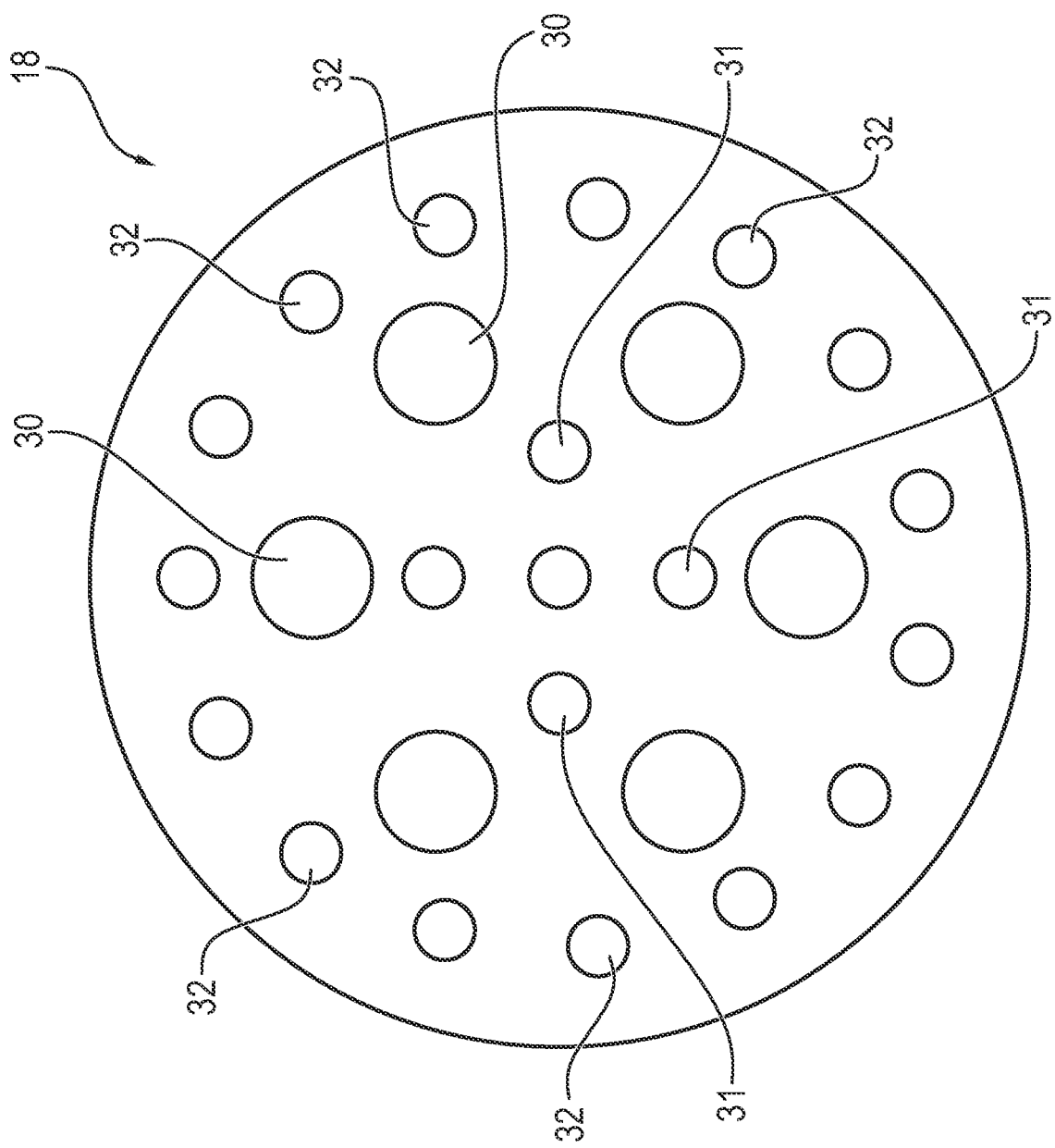
FIG. 5 is a front view showing a possible embodiment of the larger sieve of the homogenization unit.

FIG. 5 shows a different possible embodiment of the larger sieve 18. The smaller sieve 16 may have exactly the same configuration. The fluid flow direction is at right angles to the drawing plane of FIG. 5. A set of a plurality of larger holes 30, which are arranged about the center of the circular larger sieve 18, is prepared in the larger sieve 18. A set of a plurality of smaller holes 31 is arranged about the larger holes. An additional set of a plurality of smaller holes 32 is arranged between the larger holes 30 and the edge of the sieve 18. Since the holes 30 in a central area are larger than the holes 32 in an outer area, the sieve 18 reduces the volume flow in an outer area, i.e., close to the wall of the patient-side connection unit 9, more intensely than in a central area.

In one embodiment, the larger sieve 18 and the smaller sieve 16 have the same, non-rotationally symmetrical, for example, hexagonal hole pattern. These two hole patterns are, however, rotated in relation to one another about the central axis of the homogenization unit 10.

In the examples shown, the walls of the holes 29, 30, 31, 32 are at right angles to the two walls of the sieve 16, 18, which walls are parallel to one another, and thus parallel to the inner wall of the patient-side connection unit 9 at the level of the sieve 16, 18. It is also possible that the walls of the holes 29, 30, 31, 32 or at least a partial set of these holes are at an angle to the inner wall and as a result deflect the stream of fluid.

In the exemplary embodiment, the patient-side connection unit 9 and the homogenization unit 10 together form a mechanical coding. Thanks to this mechanical coding, the homogenization unit 10 can be inserted into the patient-side connection unit 9 only in a single defined rotation position. This forced and ensured rotation position ensures that the position of the holes and thus flow conditions in the sieve 16, 18 are always the same and thus reproducible. During the construction of the sieves 16 and 18, flow simulations are performed, and thanks to the forced and stationary rotation position, the real flow conditions correspond relatively well to the simulated flow conditions. Moreover, the connection between the sought volume flow and the measurable difference between the pressures in the two lines 16a and 16b can be determined in a reproducible manner in tests and can be used for the operation of the connection device.

Various types of this mechanical coding are possible.

Figure 6B:
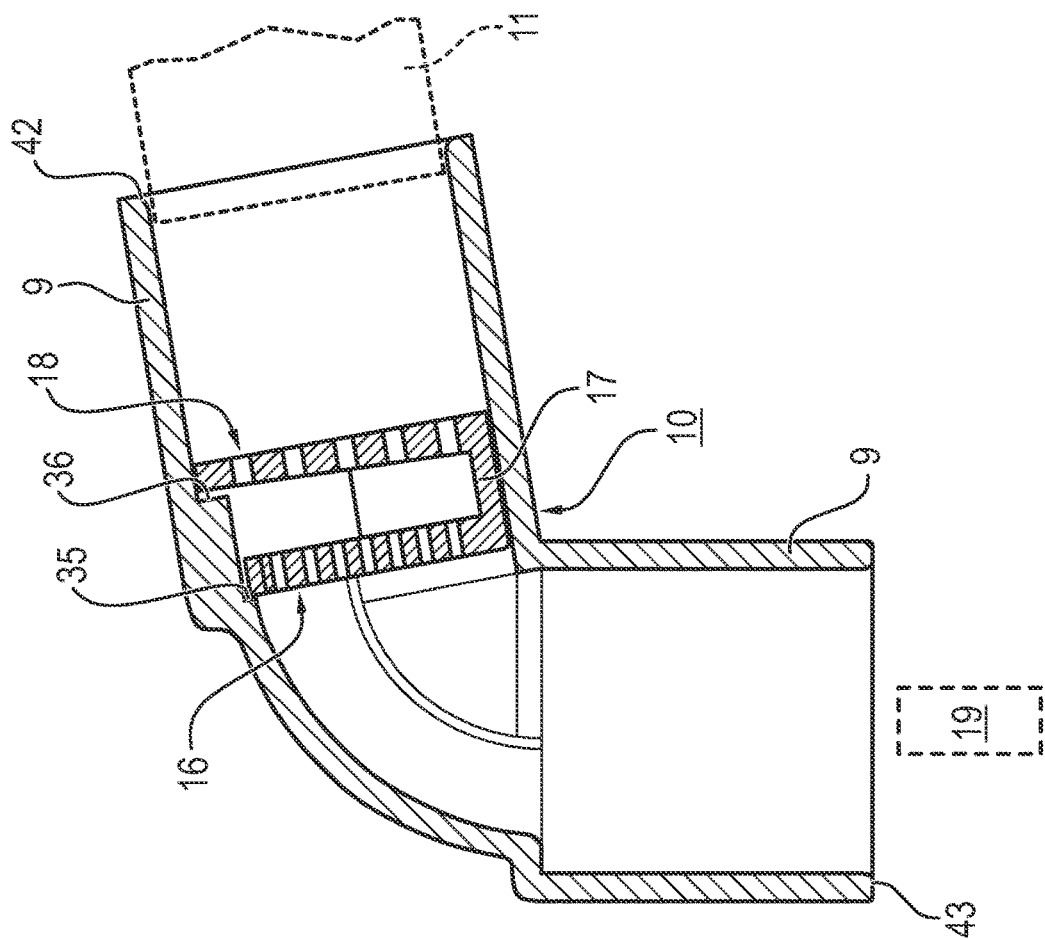
FIG. 6b is a sectional view showing how the homogenization unit from FIG. 4 is inserted into the patient-side connection unit.
Figure 6A:
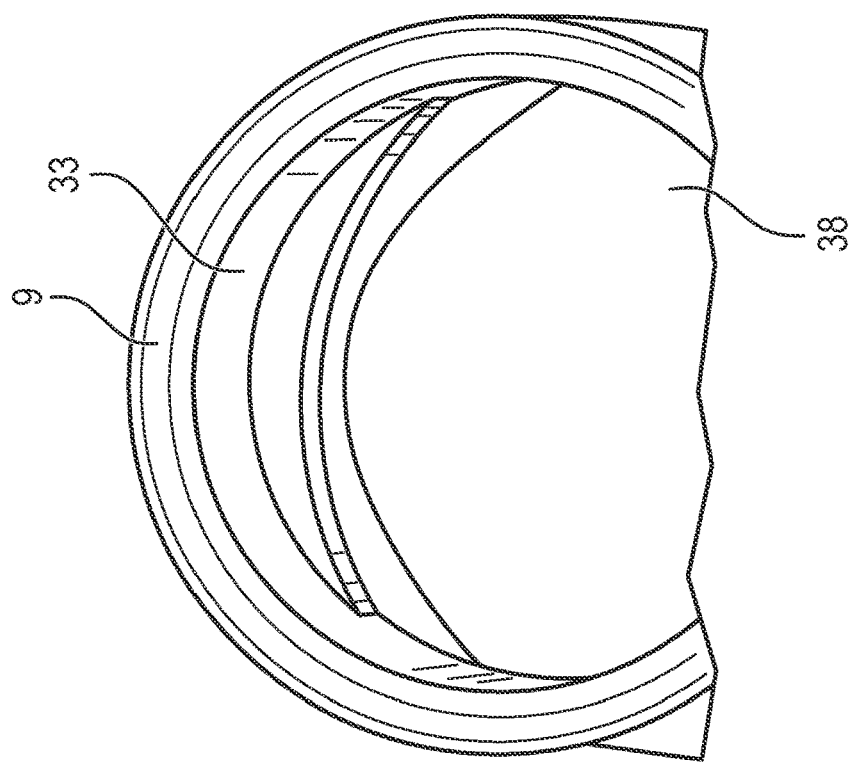
FIG. 6a is a partial perspective view showing how the homogenization unit from FIG. 4 is inserted into the patient-side connection unit.

FIG. 4 and FIG. 6a) show a possible embodiment of this mechanical coding. While the larger sieve 18 is circular, the diameter of the smaller sieve 16 varies over the circumference. The outer profile of the smaller sieve 16 comprises a flattened segment 34 and a circular arc-shaped segment 37, cf. FIG. 4. The flattened segment 34 preferably has the shape of a segment of an ellipse and especially of a circle, but with a larger diameter than the segment 37. A corresponding flattened segment 33 and a circular arc-shaped segment 38 are formed at the inner profile of the patient-side connection unit 9, cf. FIG. 6a. The fluid flow direction is at right angles to the drawing plane of FIG. 6a.

FIG. 6b shows a cross section through the patient-side connection unit 9 with a homogenization unit 10 inserted. The fluid flow direction is in the drawing plane of FIG. 6b. The patient-side connection unit 9 has a device-side end 42 and a patient-side end 43. A rear stop element 35 and a front stop element 36 are arranged in the inner profile of the patient-side connection unit 9. The terms "rear" and "front" refer to a viewing direction from the tube 11 and towards the patient P, i.e., from the device-side end 42 to the patient-side end 43.

The homogenization unit 10 is inserted into the patient-side connection unit 9 from the device-side end 42 in the exemplary embodiment, wherein the smaller sieve 16 is located in the front and the larger sieve 18 is located in the rear. During the insertion, the homogenization unit 10 is moved towards the patient-side end 43 of the connection unit 9 until the smaller sieve 16 butts against the rear stop element 35 and/or the larger sieve 18 butts against the front stop element 36, depending on which event occurs first. The just described mechanical coding ensures that the homogenization unit 10 is inserted in the correct rotation position or in a correct rotation position.

It is also possible that the outer profile of the smaller sieve 16 has a plurality of flattened segments 33 and the inner profile has a corresponding configuration.

In another configuration of the mechanical coding, the outer profile of at least one sieve 16, 18 has a projection. The inner profile of the patient-side connection unit 9 has a corresponding recess, e.g., a groove. This corresponding recess preferably tapers in a direction towards the patient-side end of the patient-side connection unit 9. The projection at a sieve 16, 18 engages with the corresponding recess during the insertion of the homogenization unit 10. During the insertion, the tapering recess guides the homogenization unit 10 and rotates it into a defined rotation position as needed. It is possible that the outer profile of the sieve 16 or 18 has a plurality of equally shaped projections and the inner profile has a plurality of equally shaped recesses, so that a plurality of rotation positions are possible.

The steps of a process for manufacturing the connection device of the exemplary embodiment are described below as an example.

The components of the connection device are manufactured and formed. In one embodiment, all components of the connection device, except for the pressure-measuring unit 101 and the display unit 1, are manufactured by molding, especially by injection molding, and by 3D printing in another embodiment.

First, the homogenization unit 10 is preferably inserted into the patient-side connection unit 9, and subsequently the tube 11 is connected in a fluid-tight manner to the patient-side connection unit 9. The homogenization unit is preferably inserted from the device-side end 42, i.e., from the end of the patient-side connection unit 9, which points towards the tube 11, and is moved towards the patient-side end. The stop elements 35 and 36 limit this movement.

During the insertion a force is exerted onto the homogenization unit 10 manually or by an automatic production machine. This force acts in the direction of the stop elements 35 and 36. This force overcomes a friction force between the homogenization unit 10 and the inner wall of the patient-side connection unit 9, and this friction force counteracts the insertion. In some embodiments of the mechanical coding, this exerted force ensures that the homogenization unit 10 is rotated into the correct position in relation to the patient-side connection unit 9, while the homogenization unit 10 is moved towards the stop elements 35 and 36, and actually reaches at least one stop element 35 and 36.

In one embodiment, the current force, which is to be overcome by inserting the homogenization unit 10 in order to move the homogenization force 10 even farther, is repeatedly measured during the insertion. As soon as the homogenization unit 10 reaches the stop elements 35 and 36, then this measured force reaches a predefined threshold. In case this measured force reaches this predefined threshold before expiration of a predefined time period, then it is certain that the homogenization unit 10 is inserted into the patient-side coupling unit 9 in an incorrect rotation position and this incorrect position can no longer be corrected by an additional force effect. In one embodiment, the homogenization unit is again removed from the patient-side connection unit 9 and reinserted.

While specific embodiments of the invention have been shown and described in detail to illustrate the application of the principles of the invention, it will be understood that the invention may be embodied otherwise without departing from such principles.

LIST OF REFERENCE CHARACTERS

1 Display unit of the volume flow sensor
2a Diaphragm in the tube 11 for linearizing the sensor characteristic curve, is open in the inhalation direction
2b Diaphragm in the tube 11 for linearizing the sensor characteristic curve, is open in the exhalation direction
3 Exhalation valve, arranged in the tube 11, comprises the exhalation opening 4 and the diaphragm 5
4 Exhalation opening in the exhalation valve 3
5a Diaphragm in the exhalation valve 3 for closing the exhalation opening 4, is in the closing position
5b Diaphragm in the exhalation valve 3 for closing the exhalation opening 4, is in the open position
6a Recoil diaphragm in the tube 11, separates the inhalation branch from the exhalation branch, is in the open position
6b Recoil diaphragm in the tube 11, separates the inhalation branch from the exhalation branch, is in the closed position
7 Pneumatic control line, forwards the airway pressure to the diaphragm 5 during the inhalation and closes this diaphragm (position 5a)
8 Opening in the exhalation valve 3, in order to release air during the exhalation
9 Angular patient-side connection unit, connected to the patient-side coupling unit 19, accommodates the homogenization unit 10, has the device-side end 42 and the patient-side end 43
10 Homogenization unit, inserted into the patient-side connection unit 9, comprises the sieves 16 and 18 and the connection element 17
11 Tube, connects the hose 15 in a fluid-tight manner to the patient-side connection element 9, comprises the two tube sections 26 and 28
12 Patient-side housing half in the tube 11, connected to the tube section 26
13a, 13b Pneumatic lines of the volume flow sensor 1, lead from the tube 11 to the pressure-measuring unit 101
14 Ventilator-side housing half in the tube 11
15 Hose, connects the ventilator 100 in a fluid-tight manner to the tube 11
16 Smaller sieve of the homogenization unit 10
17 Mechanical connection element between the two sieves 16 and 18
18 Larger sieve of the homogenization unit 10
19 Tube in the trachea of the patient P, connected to the patient-side connection unit 9
20 Connection surface of the tube section 26
22 Connection surface of the tube section 28
23a, 23b Guide elements, which guide a cap with the lines 13a, 13b during placement onto the tube 11
26 Tube section of the tube 11, connected to the patient-side housing half 12, comprises the connection surface 20
28 Tube section of the tube 11, connected to the ventilator-side housing half 14, comprises the connection surface 22
29 Hexagonal holes in the sieves 16 and 18
30 Larger round holes in the larger sieve 18
31 Smaller round holes in the larger sieve 18, arranged around the larger holes 30

32 Smaller round holes in the larger sieve 18, arranged between the larger holes 30 and the edge of the sieve 18
33 Flattened segment of the inner profile of the patient-side connection unit 9
34 Flattened segment of the outer profile of the smaller sieve 16
35 Rear stop element at the inner profile of the patient-side connection unit 9, limits the movement of the smaller sieve 16 in the connection unit 9 towards the patient-side end 43
36 Front stop element at the inner profile of the patient-side connection unit 9, limits the movement of the larger sieve 18 in the connection unit 9 towards the patient-side end 43
37 Circular arc-shaped segment of the outer profile of the smaller sieve 16
38 Circular arc-shaped segment of the inner profile of the patient-side connection unit 9
40*a* Opening in the tube section 26, functions as branching-off point, at which the line 13*a* branches off from the tube 11
40*b* Opening in the tube section 28, functions as branching-off point, at which the line 13*b* branches off from the tube 11
41 Arrow-shaped recess in the diaphragm 2
42 Device-side end of the patient-side connection unit 9
43 Patient-side end of the patient-side connection unit 9
44 Circumferential projection of the housing half 14, engages with a corresponding recess of the housing half 12
90 Volume flow sensor (flow sensor), comprises the diaphragm 2, the pneumatic lines 13*a* and 13*b*, the pressure-measuring unit 101 and the display unit 1
100 Ventilator, is in fluid connection with the patient-side coupling unit 19 by means of the fluid-guiding unit with the hose 15, with the tube 11 and with the patient-side connection unit 9, accommodates the pressure-measuring unit 101
101 Pressure-measuring unit of the volume flow sensor, measures the difference between the pressures in the lines 13*a* and 13*b*, is arranged in the ventilator 100
P Patient, which is being mechanically ventilated by the ventilator 100, is connected to the patient-side coupling unit 19
Sk Flow duct, which passes through the two tube sections 26 and 28 and through the two housing halves 12 and 14

What is claimed is:

1. A connection device for a medical arrangement, the connection device comprising:
   a fluid-guiding unit configured for establishing a fluid connection between a patient-side coupling unit that is coupleable with the patient and the medical arrangement;
   a volume flow sensor comprising an engaging component, which engages with an interior of the fluid-guiding unit wherein the volume flow sensor is configured for measuring an indicator of the volume flow of fluid through the fluid-guiding unit; and
   a homogenization unit non-rotatably inserted into the interior of the fluid-guiding unit and at a position between the patient-side coupling unit and the engaging component, the homogenization unit being configured for homogenizing a flow of fluid through the fluid-guiding unit, the homogenization unit comprising two sieves and a connection element, the two sieves being configured to homogenize the flow of fluid through the fluid-guiding unit, wherein the fluid is configured to flow through each of the sieves only at defined points, wherein the two sieves, viewed in a direction of flow through the fluid-guiding unit, are arranged behind one another and spaced apart from one another and are fixedly and permanently connected to one another by the connection element, wherein an inner profile of the fluid-guiding unit and an outer profile of the homogenization unit together form a mechanical coding, which determines a defined rotational position of the homogenization unit in relation to the fluid-guiding unit, wherein each sieve of the homogenization unit is configured to increase a degree of homogenization of the fluid flow, as compared with the device without sieves, wherein the fluid-guiding unit comprises a bent fluid-guiding element and a linear fluid-guiding element, the engaging component engaging with an interior of the linear fluid-guiding element, the homogenization unit being inserted into an interior of the bent fluid-guiding element.

2. The connection device in accordance with claim 1, wherein at least one of the two sieves of the homogenization unit has the outer profile, which together with the inner profile of the fluid-guiding unit, forms the mechanical coding, wherein a shape of one of the two sieves is different from a shape of the other one of the two sieves.

3. The connection device in accordance with claim 1, wherein:
   at least one of the two sieves has the outer profile and the fluid-guiding unit has the inner profile;
   the outer profile comprises at least one circular segment and at least one flattened segment;
   the inner profile comprises inner profile segments, which correspond to the segments of the outer profile; and
   the outer profile and the inner profile together form the mechanical coding.

4. The connection device in accordance with claim 1, wherein:
   at least one of the two sieves comprises a projection;
   the fluid-guiding unit comprises an inner profile with a recess;
   the projection engages with the recess of the inner profile; and
   the projection and the recess together form the mechanical coding.

5. The connection device in accordance with claim 1, wherein:
   at least one of the two sieves has, relative to a central axis thereof, an inner area with a first set of holes and an outer area with a second set of holes; and
   a maximum dimension of one hole of the first set of holes is greater than a maximum dimension of one hole of the second set of holes.

6. The connection device in accordance with claim 1, further comprising a stop element mounted in the interior of the fluid-guiding unit, which limits a movement of the homogenization unit towards the patient-side coupling unit.

7. The connection device in accordance with claim 1, wherein the homogenization unit is configured as a single, one-piece component, the fluid-guiding unit having a bent fluid-guiding element inner surface defining an interior space of the bent fluid-guiding element, each of the sieves being located in the interior space, each of the sieves comprising a surface configured to be in contact with the inner surface of the bent fluid-guiding element.

8. The connection device in accordance with claim 1, wherein:

the volume flow sensor comprises two pneumatic lines and a pressure-measuring unit;

each of the two pneumatic lines establishes a respective fluid connection between the fluid-guiding unit and the pressure-measuring unit;

the two pneumatic lines branch off from the fluid-guiding unit at two branching-off points;

viewed in a flow direction through the fluid-guiding unit the two branching-off points are arranged behind one another;

the engaging component is arranged between the two branching-off points; and the pressure-measuring unit is configured for measuring an indicator of a difference between the pressures in the two pneumatic lines.

9. The connection device according to claim 1, wherein one of the two sieves has a first diameter, the other one of the two sieves having a second diameter, the first diameter being less than the second diameter.

10. The connection device according to claim 9, wherein the one of the two sieves comprises a shape that includes at least one circular segment and at least one elliptical segment, the other one of the two sieves comprising a circular shape, wherein the one of the two sieves is arranged in a first area of the interior of the fluid-guiding unit and the other one of the two sieves is arranged in a second area of the interior of the fluid-guiding unit, the first area having a first cross-sectional area that is less than a second cross-sectional area of the second area.

11. A ventilation system for the mechanical ventilation of a patient, the ventilation system comprising:

a ventilator;

a patient-side coupling unit couplable with the patient; and a connection device comprising:

a fluid-guiding unit configured for establishing a fluid connection between the patient-side coupling unit that is coupleable with the patient and the ventilator;

a volume flow sensor comprising an engaging component, which engages with an interior of the fluid-guiding unit and is configured for measuring an indicator of the volume flow of fluid through the fluid-guiding unit; and a homogenization unit non-rotatably inserted into the interior of the fluid-guiding unit and at a position between the patient-side coupling unit and the engaging component, the homogenization unit being configured for homogenizing a flow of fluid through the fluid-guiding unit and comprising two sieves and a connection element, wherein the two sieves, viewed in a direction of flow through the fluid-guiding unit, are arranged behind one another and spaced apart from one another and are fixedly and permanently connected to one another by the connection element, the two sieves being configured to homogenize the flow of fluid through the fluid-guiding unit, wherein the fluid is configured to flow through each of the sieves only at defined points, wherein the fluid-guiding unit is configured to establish a fluid connection between the patient-side coupling unit and the ventilator, wherein an inner profile of the fluid-guiding unit and an outer profile of the homogenization unit together form a mechanical coding, which determines a defined rotational position of the homogenization unit in relation to the fluid-guiding unit, wherein each sieve of the homogenization unit is configured to increase a degree of homogenization of the fluid flow, as compared with the device without sieves, wherein the fluid-guiding unit comprises a bent fluid-guiding element and a linear fluid-guiding element, the engaging component engaging with an interior of the linear fluid-guiding element, the homogenization unit being inserted into an interior of the bent fluid-guiding element.

12. The ventilation system according to claim 11, wherein one of the two sieves has a first diameter, the other one of the two sieves having a second diameter, the first diameter being less than the second diameter.

13. A monitoring system for monitoring an intrinsic breathing activity of a patient, the monitoring system comprising:

a patient monitor;

a patient-side coupling unit couplable with the patient; and a connection device comprising:

a fluid-guiding unit configured for establishing a fluid connection between the patient-side coupling unit that is coupleable with the patient and the patient monitor;

a volume flow sensor comprising an engaging component, which engages with an interior of the fluid-guiding unit and is configured for measuring an indicator of the volume flow of fluid through the fluid-guiding unit; and a homogenization unit non-rotatably inserted into the interior of the fluid-guiding unit and at a position between the patient-side coupling unit and the engaging component, the homogenization unit being configured for homogenizing a flow of fluid through the fluid-guiding unit and comprising two sieves and a connection element, wherein the two sieves, viewed in a direction of flow through the fluid-guiding unit, are arranged behind one another and spaced apart from one another and are fixedly and permanently connected to one another by the connection element, the two sieves being configured to homogenize the flow of fluid through the fluid-guiding unit, wherein the fluid is configured to flow through each of the sieves only at defined points, wherein the fluid-guiding unit is configured to establish a fluid connection between the patient-side coupling unit and the patient monitor, wherein an inner profile of the fluid-guiding unit and an outer profile of the homogenization unit together form a mechanical coding, which determines a defined rotational position of the homogenization unit in relation to the fluid-guiding unit, wherein each sieve of the homogenization unit is configured to increase a degree of homogenization of the fluid flow, as compared with the device without sieves, wherein the fluid-guiding unit comprises a bent fluid-guiding element and a linear fluid-guiding element, the engaging component engaging with an interior of the linear fluid-guiding element, the homogenization unit being inserted into an interior of the bent fluid-guiding element.

14. The monitoring system according to claim 13, wherein one of the two sieves has a first diameter, the other one of the two sieves having a second diameter, the first diameter being less than the second diameter.

15. The monitoring system according to claim 14, wherein the one of the two sieves comprises a shape that includes at least one circular segment and at least one elliptical segment, the other one of the two sieves comprising a circular shape, the one of the two sieves being arranged in a first area of the interior of the fluid-guiding unit and the other one of the two sieves being arranged in a second area of the interior of the fluid-guiding unit, the first area having a first cross-sectional area that is less than a second cross-sectional area of the second area.

16. A manufacturing process comprising the steps of:
manufacturing a connection device comprising: a fluid-guiding unit configured for establishing a fluid connection between a patient-side coupling unit that is coupleable with the patient and a medical arrangement; a volume flow sensor comprising an engaging component, which engages with an interior of the fluid-guiding unit and is configured for measuring an indicator of the volume flow of fluid through the fluid-guiding unit; and a homogenization unit non-rotatably inserted into the interior of the fluid-guiding unit and at a position between the patient-side coupling unit and the engaging component, the homogenization unit being configured for homogenizing a flow of fluid through the fluid-guiding unit and comprising two sieves and a connection element, wherein the two sieves, viewed in a direction of flow through the fluid-guiding unit, are arranged behind one another and spaced apart from one another and are fixedly and permanently connected to one another by the connection element, the two sieves being configured to homogenize the flow of fluid through the fluid-guiding unit, wherein the fluid is configured to flow through each of the sieves only at defined points, wherein the fluid-guiding unit is configured to establish a fluid connection between the patient-side coupling unit and the patient monitor, wherein an inner profile of the fluid-guiding unit and an outer profile of the homogenization unit together form a mechanical coding, which determines a defined rotational position of the homogenization unit in relation to the fluid-guiding unit, wherein each sieve of the homogenization unit is configured to increase a degree of homogenization of the fluid flow, as compared with the device without sieves, the fluid-guiding unit comprising a bent fluid-guiding element and a linear fluid-guiding element, the engaging component engaging with an interior of the linear fluid-guiding element, the homogenization unit being inserted into an interior of the bent fluid-guiding element, wherein the manufacturing of the connection device comprises:
providing the volume flow sensor comprising the engaging component;
forming the homogenization unit; forming the bent fluid-guide element, which is configured to be connected to the patient-side coupling unit, and forming the linear fluid-guiding element;
inserting the engaging component of the volume flow sensor into the linear fluid-guiding element such that the engaging component engages with the linear fluid-guiding element;
inserting the homogenization unit into an inside of the bent fluid-guide element; and
after the insertions, connecting the bent fluid-guide element fluid-tight to the linear fluid-guide element to form the fluid-guiding unit of the connection device or a portion of the fluid-guiding unit.

17. A manufacturing process in accordance with claim 16, further comprising the steps of:
upon a predefined time period having passed after initiating the step of inserting the homogenization unit into the bent fluid-guide element, measuring an indicator of a force that is necessary for a further movement of the homogenization unit in relation to the bent fluid-guide element; and
determining that the homogenization unit is inserted incorrectly into the bent fluid-guide element when the measured force is above a predefined threshold.

18. A manufacturing process according to claim 16, further comprising providing a computer program, which is configured for actuating a 3D printer such that the 3D printer, as a response to the actuation, produces the fluid-guiding unit and the homogenization unit of the connection device.

19. A manufacturing process according to claim 16, further comprising providing a 3D printer, which is configured for producing the fluid-guiding unit and the homogenization unit of the connection device.

* * * * *